United States Patent [19]
Hupperts et al.

[11] Patent Number: 6,124,504
[45] Date of Patent: Sep. 26, 2000

[54] PROCESS FOR PREPARING 4-HYDROXYANILINES

[75] Inventors: Achim Hupperts, Düsseldorf; Karl Steinbeck; Uwe Stelzer, both of Burscheid; Reinhard Lantzsch, Wuppertal; Hermann Seifert, Bergisch Gladbach, all of Germany

[73] Assignee: Bayer Aktiengesellschaft, Leverkusen, Germany

[21] Appl. No.: 08/883,672

[22] Filed: Jun. 27, 1997

[30] Foreign Application Priority Data

Jul. 8, 1996 [DE] Germany .................. 196 27 424

[51] Int. Cl.⁷ .................................................. C07C 209/00
[52] U.S. Cl. ...................... 564/415; 534/843; 534/845; 534/853
[58] Field of Search .................... 534/843, 838, 534/839, 853, 845; 564/415

[56] References Cited

U.S. PATENT DOCUMENTS 2,362,508 11/1944 Stevens .

FOREIGN PATENT DOCUMENTS 2487832 2/1982 France .
4040853 6/1992 Germany .

OTHER PUBLICATIONS

STN online abstract (AN 125:195105), 1996.
Radu et al., Revista De Chimie 47 (5) pp. 411–415, 1996.
M. Shivukula, App. Environ. Microb. 61(12) 4374–7 (Dec. 1995).
Journal of Medicinal Chemistry, vol. 30, No. 3, Mar. 1987, pp. 473–479.
Chemical Abstract, vol. 125, No. 15, Oct. 7, 1996, Abstract No. 195105t, "Synthesis of some active physiological properties by condensation of sodium 4–(phenylazo) phenoxides with monochloroacetic acid." p. 1155.
Chemical Abstract, vol. 124, No. 5, Jan. 29, 1996, Abstract No. 49140p, "Phenolic azo dye oxidation by laccase from pyricularia oryzae", p. 531.
P. Bosshard, et al. Helvetica Chimica Acta, Bd. 47, Nr. 3, Apr. 20, 1964, pp. 769–784.

*Primary Examiner*—Samuel Barts
*Attorney, Agent, or Firm*—Norris, McLaughlin & Marcus, P.A.

[57] ABSTRACT

The application describes a process for preparing 4-hydroxyanilines by the reaction of phenols with diazonium salts and subsequent reduction.

14 Claims, No Drawings

PROCESS FOR PREPARING 4-HYDROXYANILINES

The application relates to the preparation of 2,3-disubstituted 4-hydroxyanilines by the reaction of 2,3-disubstituted phenols with diazonium salts and subsequent reduction.

2,3-Disubstituted 4-hydroxyanilines are important intermediates for preparing crop protection agents and are described in DE-4 040 853.

A novel process for preparing 2,3-disubstituted 4-hydroxyanilines has now been found which has very high and reproducible yields, simple purification and work-up steps and gentle reaction conditions and in which no byproducts and inactive isomers are formed.

The application accordingly provides a process for preparing compounds of the formula (I)

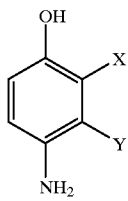
(I)

in which

X and Y independently of one another each represent halogen, alkoxy and CN by reacting
a) phenols of the formula (II)

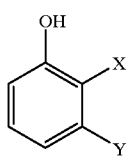
(II)

in which

X and Y are as defined above
with diazonium salts of the formula (III)

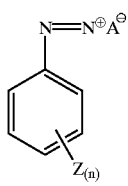
(III)

in which n represents a number 0 to 5,

Z represents halogen, alkyl, $NO_2$, COOH, CN and $SO_3H$, Z in the case of $n \geq 2$ optionally having different meanings $A^-$ represents a counterion
and
b) subsequent reduction of the diazene of the formula (IV)

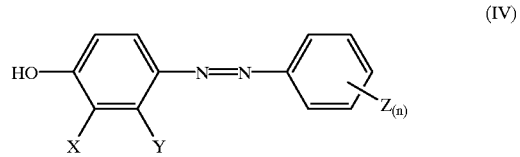
(IV)

obtainable by process step a) to give the target compound.

The process step a) is preferably carried out by adding a solution of the diazonium salts of the formula (III) to an aqueous solution of the phenols of the formula (II). The reaction is carried out at temperatures from 0 to 50° C., preferably 0 to 20° C. The pH value of the solution is preferably higher than the pKs value of the phenol of the formula (II).

The mixture is then adjusted to a pH value $\leq 7$ preferably using mineral acids, and the diazene of the formula (IV) is extracted by extraction with an organic solvent not miscible with water, such as, for example, ethyl acetate or butanol.

The process step b) is preferably carried out by hydrogenating the diazene of the formula (IV) obtainable by process step a) in the presence of inert solvents such as, preferably, water, alcohols such as methanol, ethanol or butanol, hydrocarbons such as, for example, toluene or dioxane, pyridine, dimethylformamide or mixtures of these solvents.

The reaction solution obtained by process a) is preferably reacted directly according to process b) without any further purification.

The hydrogenation is preferably carried out using hydrogen or hydrazines in the presence of a catalyst and, if appropriate, in the presence of auxiliaries, or using metals or metal salts in the presence of acids, or using sodium dithionite or hydroiodic acid. If required, the reaction solution has to be neutralized (pH~7) with mineral acids prior to the hydrogenation.

Preferred embodiments of the hydrogenation and in particular catalysts and auxiliaries are described in DE-4 428 535 which is incorporated into the present application by reference. Preference is given to a process for the catalytic hydrogenation in the presence of catalysts characterized in that the hydrogenation is carried out in the liquid phase and in the presence of a catalyst comprising at least one metal or one metal compound from the group consisting of nickel, cobalt and the noble metals and in the presence of at least one sulpho compound of the formula (V)

(V)

in which $R^1$ and $R^2$ independently of one another each represent straight-chain or branched $C_1$–$C_{12}$-alkyl, hydroxy$C_1$–$C_{12}$-alkyl, carboxy-$C_1$–$C_{12}$-alkyl or phenyl, $R^1$ may additionally represent hydrogen or CO—$C_1$–$C_{12}$-alkyl $R^1$ and $R^2$ together may also represent —CH=CH—CH=CH—, —$(CH_2)_4$—, —$(CH_2)_5$— or —$(CH_2)_2$—X—$(CH_2)_2$ where X=oxygen or sulphur and n represents zero or 1.

Preferred sulphur compounds of the formula (V) are those in which $R^1$ and $R^2$ are identical and represent hydroxy-$C_1$–$C_6$-alkyl. Very particular preference is given to bis-(2-hydroxyethyl) sulphide.

Suitable noble metals for the catalyst are, for example, ruthenium, rhodium, palladium, osmium, iridium and platinum. Preference is given to platinum. Nickel, cobalt, noble metals or compounds thereof may optionally be present on a carrier. A preferred carrier material is carbon.

The amount of the catalyst is not critical and may be varied within wide limits. For example, 0.02 to 3% by weight, preferably 0.1 to 1% by weight, of noble metal catalyst, based on the compound of the formula (IV) may be used.

The weight ratio of sulphur compound of the formula (V) to catalyst may be, for example, 0.001 to 0.125:1. Preferably, the weight ratio is from 0.0025 to 0.025:1, particularly preferably from 0.005 to 0.0125:1.

The sulphur compounds of the formula (V) may be used as individual compounds or as mixtures of various individual compounds. Preference is given to using the sulphur compounds in the form of solutions. They may be added to the reaction mixture for example in the form of a 0.01 to 1% strength by weight solution in water or toluene. It is also possible to mix the sulphur compounds with the catalyst prior to the reaction.

Particularly preferably the hydrogenation is carried out using hydrogen or hydrazine hydrate in the presence of Raney nickel and bis(2-hydroxyethyl) sulphide or using iron powder or zinc powder in the presence of hydrochloric acid.

The reaction temperatures are preferably 0 to 150° C., in particular 10 to 50° C. The reaction is preferably carried out at pressures of 1 to 100 bar, in particular 1 to 20 bar.

Work-up is carried out by conventional methods, preferably by distilling off the solvents and the aniline that may still be present, setting a suitable pH value by the addition of mineral acids or bases (pH=isoelectric point of the hydroxyaniline) and purifying the crude product by washing or recrystallization from an inert solvent, such as, for example, water or toluene.

The aniline which may have been recovered can be recycled into the process.

The amount of diazonium salt used is 1 to 1.5 mol, based on 1 mol of phenol compound. Hydrogen is generally used in twice the molar amount, based on the amount of diazene compound, an excess may be used. Metal and mineral acid are also used in at least twice the molar amount, based on the amount of diazene compound or metal, respectively.

Preference is given to using compounds of the formula (II) in which

X and Y independently of one another each represent chlorine, bromine, fluorine, methoxy, ethoxy and CN.

Particular preference is given to using compounds of the formula (II) in which

X represents chlorine and

Y represents chlorine.

Preference is given to using compounds of the formula (III) in which n represents a number 0, 1, 2 or 3 and Z represents chlorine, fluorine, bromine, $NO_2$, COOH, CN, $SO_3H$, methyl and ethyl, Z in the case of $n \geq 2$ optionally having different meanings.

Particular preference is given to using compounds of the formula (III) in which n represents the number 0.

The compounds of the formula (III) are obtained by conventional processes, for example by reacting 1 mol of aniline of the formula (IIIa)

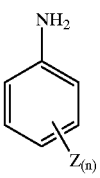

(IIIa)

in which n and Z are as defined above with 1 to 5 mol, preferably 1.5 to 2 mol, of nitrite compounds, such as for example and preferably $NaNO_2$, in dilute mineral acids, such as, for example, 15% strength hydrochloric acid, at 0 to 10° C.

The process according to the invention affords 2,3-disubstituted 4-hydroxyanilines in good yield with high selectivity and purity. It is very surprising that in process step a), with the given substitution pattern, reaction takes place exclusively at the position para to the OH group.

The application also provides the compounds of the formula (IV) obtainable by process a) in which X Y, Z and n are each as defined above.

The invention is illustrated by the examples below. The invention is not limited to the examples.

EXAMPLE 1

At 0 to 5° C., a solution of 7.6 g (0.11 mol) of $NaNO_2$ in 12 ml of $H_2O$ is added dropwise to 50 ml of aqueous HCl (15%) and 9.8 g (0.105 mol) of aniline in a 100 ml two-neck flask fitted with internal thermometer and magnetic stirrer. After 10 minutes, this diazonium salt solution is added at 5 to 10° C. to a solution of 16.3 g (0.1 mol) of 2,3-dichlorophenol and 20 g (0.5 mol) of NaOH in 200 ml of $H_2O$. The mixture is allowed to warm to room temperature, stirred for an additional 4 hours, neutralized with aqueous HCl and extracted 3× with 100 ml of ethyl acetate each. The combined organic phases are washed with NaCl solution and dried with $Na_2SO_4$, and the solvent is distilled off using a rotary evaporator. 31.8 g of (2,3-dichloro-4-hydroxyphenyl)phenyldiazene are obtained.

Recrystallization from 200 ml of toluene and 10 ml of methanol affords 25.8 g (96.6% of theory) of the pure diazene (melting point: 277–279° C.).

EXAMPLE 2

In a 500 ml three-neck flask fitted with internal thermometer, stirrer and gas inlet tube, 31.8 g (0.1 mol) of non-purified (2,3-dichloro-4-hydroxyphenyl)phenyldiazene as obtained from Example 1 are dissolved in 350 ml of methanol with gentle warming. The flask is flushed with argon, and 5 g of Raney nickel and 25 μl of bis(2-hydroxyethyl) sulphide are then added. At room temperature, 4640 ml (0.2 mol) of hydrogen are then applied with a pressure of about 1 bar over 2.5 hours. The reaction mixture is admixed with a little activated charcoal, stirred for a further 15 minutes and filtered over a bed of silica gel. Removal of the solvent by distillation affords 28.3 g of crude product. By heating the crude product with 100 ml of toluene, filtration with suction and drying of the solid, 17.0 g (95.5% of theory) of pure 4-hydroxy-2,3-dichloroaniline can be isolated (melting point: 148–150° C.).

EXAMPLE 3

In a 50 ml two-neck flask fitted with internal thermometer and stirrer, 3.18 g (0.01 mol) of non-purified (2,3-dichloro- 4-hydroxyphenyl)phenyldiazene as obtained from Example 1 are dissolved in 20 ml of methanol with gentle warming. 1.12 g (0.02 mol) of iron powder are added, and 3.5 ml (0.04 mol) of concentrated aqueous HCl are slowly added dropwise at room temperature. The suspension is stirred at room temperature for 30 minutes and then neutralized with NaOH and extracted with 3×10 ml of ethyl acetate. The combined organic phases are dried with $Na_2SO_4$, and the solvent is distilled off using a rotary evaporator to give 2.01 g of crude product. By heating with 10 ml of toluene, filtration with suction and drying of the solid, 1.62 g (91.0% of theory) of pure 4-hydroxy-2,3-dichloroaniline can be isolated (melting point: 148–150° C.).

EXAMPLE 4

At 0 to 5° C., a solution of 7.6 g (0.11 mol) of $NaNO_2$ in 12 ml of $H_2O$ is added dropwise to 50 ml of aqueous HCl (15%) and 17.0 g (0.105 mol) of 2,3-dichloroaniline in a 100 ml two-neck flask fitted with internal thermometer and magnetic stirrer. After 10 minutes, this diazonium salt solution is added at 5 to 10° C. to a solution of 16.3 g (0.1 mol) of 2,3-dichlorophenol and 20 g (0.5 mol) of NaOH in 200 ml of $H_2O$. The mixture is allowed to warm to room temperature, stirred for an additional 4 hours, neutralized with aqueous HCl and extracted 3× with 200 ml of ethyl acetate each. The combined organic phases are filtered through diatomaceous earth, washed with NaCl solution and dried with $Na_2SO_4$, and the solvent is distilled off using a rotary evaporator. 29.5 g of diazene are obtained. Recrystallization from 200 ml of toluene affords 28.9 g (86% of theory) of pure (2,3-dichloro-4-hydroxyphenyl)-2,3-dichlorophenyldiazene (melting point 197–199° C.).

EXAMPLE 5

At 0 to 5° C., a solution of 7.6 g (0.11 mol) of $NaNO_2$ in 12 ml of $H_2O$ is added dropwise to 50 ml of aqueous HCl (15%) and 18.1 g (0.105 mol) of sulphanilic acid in a 100 ml two-neck flask fitted with internal thermometer and magnetic stirrer. After 1 hour, this diazonium salt suspension is added at 5 to 10° C. to a solution of 16.3 g (0.1 mol) of 2,3-dichlorophenol and 20 g (0.5 mol) of NaOH in 200 ml of $H_2O$. The mixture is allowed to warm to room temperature, stirred for a further 4 hours and neutralized with aqueous HCl, and the precipitated solid is filtered off with suction using a suction filter. Recrystallization from 200 ml of toluene and 20 ml of methanol affords 26.3 g (83.5% of theory) of pure (2,3-dichloro-4-hydroxyphenyl)-4-sulphonylphenyldiazene.

EXAMPLE 6

At 0 to 5° C., a solution of 3.8 g (0.055 mol) of $NaNO_2$ in 6 ml of $H_2O$ is added dropwise to 25 ml of aqueous HCl (15%) and 4.9 g (0.0525 mol) of aniline in a 100 ml two-neck flask fitted with internal thermometer and magnetic stirrer. After 10 minutes, this diazonium salt solution is added at 5 to 10° C. to a solution of 8.15 g (0.05 mol) of 2,3-dichlorophenol and 10 g (0.25 mol) of NaOH in 100 ml of $H_2O$. The mixture is allowed to warm to room temperature, stirred for a further 1 hour and neutralized with aqueous HCl (pH=7). In a 500 ml three-neck flask fitted with internal thermometer, stirrer and gas inlet tube, this solution is admixed with 300 ml of methanol, 2.5 g of Raney nickel and 15 µl of bis(2-hydroxyethyl) sulphide, and the flask is flushed with argon. At 40 to 50° C., 2300 ml of hydrogen (0.1 mol) are then applied with a pressure of about 1 bar over 1.5 hours. The reaction mixture is admixed with a little activated charcoal, stirred for a further 15 minutes and filtered over a bed of silica gel. The methanol is distilled off and pure 4-hydroxy-2,3-dichloroaniline precipitates from the aqueous solution, giving a yield of 83%.

EXAMPLE 7

At 0–5° C., a solution of 3.8 g (0.055 mol) of $NaNO_2$ in 6 ml of $H_2O$ is added dropwise to 25 ml of aqueous HCl (15%) and 4.9 g (0.0525 mol) of aniline in a 100 ml two-neck flask fitted with internal thermometer and magnetic stirrer. After 10 minutes, this diazonium salt solution is added at 5 to 10° C. to a solution of 8.15 g (0.05 mol) of 2,3-dichlorophenol and 10 g (0.25 mol) of NaOH in 100 ml of $H_2O$. The mixture is allowed to warm to room temperature, stirred for a further 1 hour and neutralized with aqueous HCl (pH=7). In a 500 ml three-neck flask fitted with internal thermometer, stirrer and gas inlet tube, this solution is admixed with 300 ml of methanol, 2.5 g of Raney nickel and 15 µl of bis(2-hydroxyethyl) sulphide, and the flask is flushed with argon. At 40–50° C., 2300 ml of hydrogen (0.1 mol) are then applied with a pressure of about 1 bar over 1.5 h. The reaction mixture is admixed with activated charcoal, stirred for a further 15 min, filtered over a bed of silica gel and adjusted to pH=5.7 with aqueous HCl. The methanol is distilled off, and 8.4 g (94.4% of theory) of pure 4-hydroxy-2,3-dichloroaniline precipitate from the aqueous solution.

EXAMPLE 8

At 0–5° C., a solution of 7.3 g (0.105 mol) of $NaNO_2$ in 22 ml of $H_2O$ is added dropwise to 50 ml of aqueous HCl (15%) and 9.3 g (0.1 mol) of aniline in a 250 ml two-neck flask fitted with internal thermometer and magnetic stirrer. After 30 min, this diazonium salt solution is added slowly at 5–10° C. to a solution of 16.4 g (0.1 mol) of 2,3-dichlorophenol and 12.4 g (0.31 mol) of NaOH in 100 ml of $H_2O$. The suspension is allowed to warm to room temperature and stirred for a further 1 h, and 0.5 g of Raney nickel are then added. 6 g (0.06 mol) of hydrazine hydrate are then added at 40–50° C. over a period of 2 h. After the addition, stirring is continued for 1 h and the solution is filtered over a bed of silica gel. With cooling, the solution is then adjusted to pH=5.7 with 20% strength HCl. The precipitated solid is washed with 50 ml of water and 50 ml of toluene and dried. 16.8 g (94.3% of theory) of pure 2,3-dichloro-4-hydroxyaniline are obtained.

EXAMPLE 9

At 0–5° C., a solution of 2.9 g (0.042 mol) of $NaNO_2$ in 5 ml of $H_2O$ is added dropwise to 20 ml of aqueous HCl (15%) and 3.7 g (0.04 mol) of aniline in a 100 ml two-neck flask fitted with internal thermometer and magnetic stirrer. After 10 minutes, this diazonium salt solution is added at 5–10° C. to a solution of 5.0 g (0.038 mol) of 2,3-difluorophenol and 6.1 g (0.152 mol) of NaOH in 60 ml of $H_2O$. The solution is allowed to warm to room temperature, stirred for a further 4 h, neutralized with aqueous HCl and extracted 3× with 50 ml of ethyl acetate each. The combined organic phases are washed with NaCl solution and dried with $Na_2SO_4$, and the solvent is distilled off using a rotary evaporator. 8.4 g (94.5% of theory) of 2,3-(difluoro-4-hydroxyphenyl)phenyldiazene (melting point 141° C.) are obtained.

EXAMPLE 10

At room temperature, 3.5 g (0.015 mol) of (2,3-difluoro-4-hydroxyphenyl)-phenyldiazene are dissolved in 30 ml of methanol in a 100 ml three-neck flask fitted with internal thermometer, stirrer and gas inlet tube. The flask is flushed with argon, and 1.5 g of Raney nickel and 25 μl of bis(2-hydroxyethyl) sulphide are then added. 692 ml of hydrogen (0.03 mol) are then applied at room temperature with a pressure of about 1 bar. The reaction mixture is admixed with activated charcoal, stirred for a further 15 minutes and filtered over a bed of silica gel. The solvent is distilled off and the residue is washed with n-hexane, affording 2.0 g (91.9% of theory) of 4-hydroxy-2,3-difluoroaniline.

What is claimed is:

1. A compound of the formula (IV)

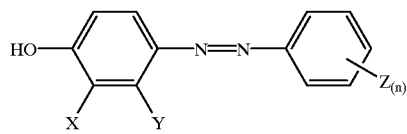

(IV)

in which

X and Y independently of one another each represent halogen, and CN n represents a number 0 to 5, Z represents halogen, alkyl, $NO_2$, CN, COOH and $SO_3H$, Z in the case of $n \geq 2$ optionally having different meanings, excluding the compound

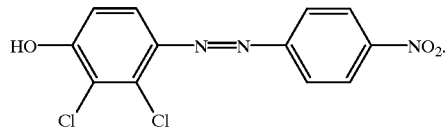

2. A compound according to claim 1 in which

X and Y independently of one another each represent chlorine, bromine, fluorine, CN, n represents a number 0, 1, 2 or 3 and Z represents chlorine, fluorine, bromine, $NO_2$, CN, COOH, $SO_3H$, methyl and ethyl, Z in the case of $n \geq 2$ optionally having different meanings.

3. A compound according to claim 1 in which

X represents chlorine and

Y represents chlorine, n represents a number 0, 1, 2 or 3 and

Z represents chlorine, fluorine, bromine, $NO_2$, CN, COOH, $SO_3H$, methyl and ethyl, Z in the case of $n \geq 2$ optionally having different meanings.

4. A compound according to claim 3 in which n represents the number 0.

5. A compound according to claim 1 in which

X and Y each represent fluorine and n represents a number 0, 1, 2 or 3 and

Z represents chlorine, fluorine, bromine, $NO_2$, CN, COOH, $SO_3H$, methyl and ethyl, Z in the case of $n \geq 7$ optionally having different meanings.

6. A compound according to claim 5 in which n represents the number 0.

7. Process for preparing compounds of the formula (IV)

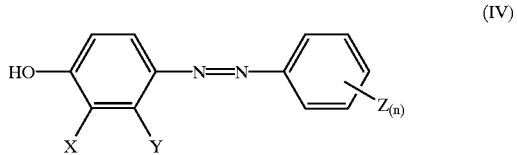

(IV)

in which X, Y, Z and n are each as defined in claim 1, characterized in that phenols of the formula (II)

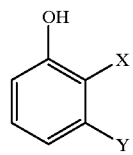

(II)

in which

X and Y are each as defined above are reacted with diazonium salts of the formula (III)

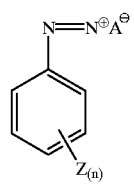

(III)

in which n represents a number 0 to 5, z represents halogen, alkyl, $NO_2$, COOH, CN and $SO_3H$, Z in the case of $n \geq 2$ optionally having different meanings, $A^-$ represents a counterion.

8. A compound according to claim 1, which is (2,3-dichloro-4-hydroxyphenyl)phenyldiazene of the formula:

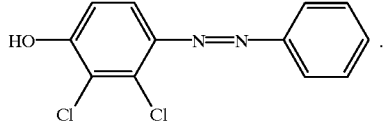

9. Process for preparing compounds of the formula (I)

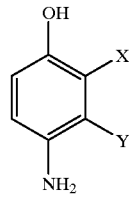

(I)

in which

X and Y independently of one another each represent halogen, and CN by reacting a) phenols of the formula (II)

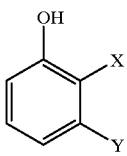

(II)

in which
X and Y are as defined above
with diazonium salts of the formula (III)

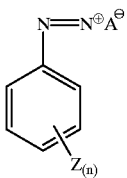

(III)

in which
n represents a number 0 to 5,
Z represents halogen, alkyl, $NO_2$, COOH, CN and $SO_3H$, Z in the case of $n \geq 2$ optionally having different meanings
$A^-$ represents a counterion
and
b) subsequent reduction of the diazene of the formula (IV) according to claim 7

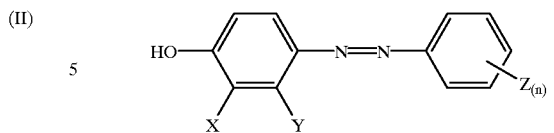

(IV)

obtainable by process step a).

10. Process according to claim 9, characterized in that the reaction of process step a) is carried out in an aqueous medium at temperatures of 0 to 50° C.

11. Process according to claim 9, characterized in that the reduction of process step b) is carried out by hydrogenation in the presence of inert solvents.

12. Process according to claim 11, characterized in that the hydrogenation is carried out using hydrogen or hydrazine hydrate in the presence of an auxiliary at temperatures of 0 to 150° C.

13. Process according to claim 9, characterized in that compounds of the formula (II) are used in which X and Y independently of one another each represent chlorine, bromine, fluorine, and CN.

14. Process according to claim 9, characterized in that compounds of the formula (III) are used in which n represents a number 0, 1, 2 or 3 and Z represents chlorine, fluorine, bromine, $NO_2$, COOH, CN, $SO_3H$, methyl and ethyl, Z in the case of $n \geq 2$ optionally having different meanings.

* * * * *